United States Patent [19]

Hartman et al.

[11] Patent Number: 5,432,056
[45] Date of Patent: Jul. 11, 1995

[54] BISULFITE-BASED TISSUE FIXATIVE

[75] Inventors: Anthony L. Hartman; Janis L. Klotz; Christine R. Jones, all of Tucson, Ariz.

[73] Assignee: Ventana Medical Systems, Inc., Tucson, Ariz.

[21] Appl. No.: 152,863

[22] Filed: Nov. 15, 1993

[51] Int. Cl.$^6$ .......................................... G01N 33/543
[52] U.S. Cl. .................. 435/7.21; 435/40.5; 435/40.52; 435/1; 435/7.23; 435/960; 435/962; 436/18; 436/826
[58] Field of Search ...................... 436/18, 826; 424/3; 435/7.21, 7.23, 1, 960, 961

[56] References Cited

U.S. PATENT DOCUMENTS

| | | | |
|---|---|---|---|
| 4,201,693 | 5/1980 | Hurt et al. | 422/61 |
| 5,225,325 | 7/1993 | Miller et al. | 424/3 |

FOREIGN PATENT DOCUMENTS 2590022  5/1987  France .

OTHER PUBLICATIONS

Kah, Olivier, et al., *The Dopaminergic Innervation of the Goldfish Pituitary*, 244 Cell and Tissue Research 577–582 (1986).

Pearse, A. G. E., Histochemistry, Theoretical and Applied 334–383 (2d ed., Little, Brown & Co. 1960).

Pearse, A. G. E., Histochemistry, Theoretical and Applied 2:850–873 (4th ed., Churchill Livingstone 1985).

Rajaofetra, N., et al. *Pre- and Post-Natal Ontogeny of Serotonergic Projections to the Rat Spinal Cord*, 22 Journal of Neuroscience Research 305–321 (1989).

Tietz, Norbert W., Fundamentals of Clinical Chemistry 926 (W. B. Saunders Co. 1976).

M. Elleder et al., Histochemie, vol. 25, pp. 286–288 (1971).

A. Sincock et al., Med. Sci. Res., vol. 18, pp. 31–32 (1990).

P. Fritz et al., Histochemistry, vol. 93, pp. 175–181 (1989).

M. Dutt, Life Sci. Adv., vol. 3, Nos. 2 and 3, pp. 138–142 (1984).

*Primary Examiner*—Mary E. Ceperley
*Attorney, Agent, or Firm*—Skjerven, Morrill, MacPherson, Franklin & Friel; Laura Terlizzi

[57] ABSTRACT

The present invention provides a bisulfite-based tissue fixative that improves morphology, antigen retention, and antigenicity. The fixative is suitable for use with sections of frozen tissue, cytology preparations (including touch preparations and blood smears) and other specimens used for immunohistochemical analysis. The fixative comprises an acidic buffer and a bisulfite salt in an effective amount for tissue fixation. In a preferred embodiment, the tissue fixative comprises a bisulfite salt in a concentration of from about 0.01 to about 0.25M, preferably, 0.02 to 0.25M, in an acidic buffer having a pH of from about 2 to about 6.

9 Claims, No Drawings

BISULFITE-BASED TISSUE FIXATIVE

FIELD OF THE INVENTION

This invention relates to a tissue fixative solution that improves morphology of non-formalin fixed tissues while retaining antigen and preserving antigenicity.

BACKGROUND OF THE INVENTION

There are two general categories of histochemical specimens. The most common is fixed, paraffin-embedded tissue specimens. These specimens are fixed, (usually using a formalin-based fixative), dehydrated to xylene, embedded in paraffin, sectioned onto a slide, deparaffinized, rehydrated, and stained. The second category includes preparations which are fresh tissues and/or cells, which generally are not fixed with aldehyde-based fixatives. Such specimens are either placed directly on a slide or coverslip, or frozen and sectioned onto slides. Such specimens are then fixed, usually with an alcohol- or acetone-based fixative, and stained. These specimens commonly include biopsy materials which may be analyzed while the surgical procedure is in progress (frozen sections), cytological preparations (including touch preparations and blood smears), and tissues which are to be immunohistochemically analyzed.

Although buffered formaldehyde-based fixative solutions at pH's of 7.0 or greater (e.g., 10% neutral buffered formalin (NBF), 1-4% paraformaldehyde, Zamboni's, Bouin's, B5, Hollande's) provide excellent results for conventional staining methods, these fixatives are problematic for use with antibody staining methods as they covalently modify and cross link the antigens. This often results in the direct alteration of the epitope(s) or epitopic accessibility, either of which prevents antibody recognition and/or binding. Thus, antibodies are unable to detect many antigens present in tissues fixed using aldehyde-based fixatives.

Fresh biopsy specimens, cytological preparations, (including touch preparations and blood smears), frozen sections and tissues for immunohistochemical analysis are commonly fixed in organic solvents (ethanol, methanol, and/or acetone). Although such fixatives do not create problems with antibody recognition due to cross linking, the fixatives do create problems of membrane extraction, nuclear lysis, and loss of antigenicity in specimens. The alcohol fixatives, while improving morphology over acetone-fixed preparations, allow significant extraction and result in greater loss of antigenicity than acetone-fixed tissues. Acetone preserves antigenicity well, but poorly preserves morphology, and allows antigens to diffuse and be extracted. Aldehyde-based fixatives can be used on nonparaffin-embedded specimens to preserve morphology and prevent extraction. However, as stated above, the aldehyde fixatives significantly destroy antigenicity and increase the difficulty of antibody penetration.

A non-aldehyde-based fixative which does not have the disadvantages of the alcohol or acetone fixatives is desirable.

SUMMARY OF THE INVENTION

The present invention provides a bisulfite-based tissue fixative that improves morphology, antigen retention, and antigenicity. The fixative is suitable for use with sections of frozen tissue, cytology preparations (including touch preparations and blood smears) and specimens used for immunohistochemical analysis. A tissue fixative of this invention comprises an acidic buffer and a bisulfite salt in an effective amount for tissue fixation. In a preferred embodiment, the fixative comprises a bisulfite salt in a concentration of from about 10 to about 250 mM, preferably about 20 to about 80 mM, in an acidic buffer having a pH of from about 2 to about 6.

The invention also provides a method for fixing tissues for immunohistochemical staining comprising contacting the tissue with a tissue fixative comprising an acidic buffer and a bisulfite salt in an effective amount for tissue fixation.

DESCRIPTION OF THE INVENTION

The present invention provides a bisulfite-based tissue fixative that improves morphology, antigen retention, and antigenicity in sections of frozen tissue, cytology preparations, and immunohistochemical preparations. The bisulfite-based tissue fixative of this invention solves the problem of membrane extraction, nuclear lysis, and loss of antigenicity in non-formalin fixed specimens with no apparent decrease in antibody accessibility. A tissue fixative of this invention comprises an acidic buffer and a bisulfite salt in an effective amount for tissue fixation.

Bisulfite

The bisulfite salt can be any bisulfite salt; e.g.; sodium bisulfite ($NaHSO_4$) or calcium bisulfite $Ca(HSO_3)_2$ or a metabisulfite which forms bisulfite in aqueous solutions. Sodium bisulfite or sodium metabisulfite are preferred. Sodium bisulfite and sodium metabisulfite are commercially available from a number of sources including Sigma Chemical Co. (St. Louis, Mo.). The bisulfite salt is present in the tissue fixative at a concentration which is effective to fix the tissue. Preferably, the bisulfite concentration is from about 10 to about 250 mM, more preferably from about 20 to about 80 mM, most preferably about 40 mM.

Buffer

The acidic buffer can be any buffer capable of maintaining an acidic pH. Preferably, the pH of the buffer is from about 2 to about 6, more preferably from about 4 to about 5, most preferably about pH 4.6. In a preferred embodiment, the acidic buffer is acetate buffer, citrate buffer, or succinate buffer in a concentration sufficient to maintain the desired pH. The pH of the bisulfite in solution is about 4.7. Therefore, maintaining the pH at 4.6 does not require much buffering capacity. However, the buffer must be sufficient to prevent the slides and tissue from altering the pH of the solution. In general, about 10 mM is sufficient.

A most preferred tissue fixative formulation consists essentially of 0.04M sodium bisulfite in 0.1M acetate buffer, pH 4.6. Preparation and use of the preferred tissue fixative is described in the examples.

The tissue fixative is prepared by mixing the appropriate concentration of the bisulfite salt in the selected acidic buffer. The tissue fixative is stored at room temperature in glass or plastic containers. When a buffer which can be stored in dry powder form is used; e.g., citrate buffer, the tissue fixative can be formulated and stored in powdered form.

Method of Fixing Tissue

The present invention also comprises a method of fixing tissue for immunohistochemical staining. The method comprises contacting the tissue with a tissue fixative of this invention.

The tissue can be a frozen section, a cytological preparation (including touch preparations and blood smears), or a needle biopsy, as described previously. Preferably, the method additionally comprises the step of contacting the tissue section with an antibody.

The fixative is used in the same manner as other fixatives, which is by immersing the tissue in the fixative. This is conveniently performed by placing the slide in a container of the fixative. However, the tissue section can be placed directly in a container of the fixative. Alternatively, the tissue fixative can be added to a slide to cover the tissue section. The antigen modification/modulation with this fixative can be carried out over a broad range of temperature with the preferred range being 20°–45° C.

The time course of the fixation for tissue sections and cytology preparations is from 5 to 120 minutes with a preferred time of 5–60 minutes. Larger tissues specimens require longer fixation times. In addition, if the bisulfite concentration is at the lower end of the concentration range; e.g., about 10 mM to about 20 mM, the fixation time can be increased. Tissues which remained in bisulfite fixative for five days have been embedded in paraffin and retain sufficient antigenicity and morphology for staining. Such tissues do not require further postfixation in formalin.

This invention is further illustrated by the following specific but non-limiting examples. Procedures which are constructively reduced to practice are described in the present tense, and procedures which have been carried out in the laboratory are set forth in the past tense.

EXAMPLE 1

Preparation of Tissue Fixative

A preferred tissue fixative of this invention was prepared as follows.

Acetate buffer was prepared by mixing 24.5 ml of 0.2 M sodium acetate with 25.4 ml of 0.2M acetic acid. The buffer was brought to 100 ml by the addition of 50 ml of distilled water giving a final molarity of 0.10M and a pH of 4.6. A total of 0.380 gm of sodium metabisulfite (Sigma Chem. Co. Cat. #S9000) was added and the mixture was stirred until the sodium bisulfite was dissolved. The solution was stored in a capped plastic bottle at room temperature.

EXAMPLE 2

Preparation of Tissue Fixative

The procedure of Example 1 was repeated using a total of 0.380 gm of sodium metabisulfite (Sigma Chemical Company; Cat. S8890). Use of the tissue provides equivalent results to those of the fixative of Example 1.

EXAMPLE 3

Fixation of Tissue

A frozen tissue section affixed to a slide was immersed in a jar containing tissue fixative prepared as described in Example 1. The section remained in the tissue for 10 minutes.

EXAMPLE 4

Fixation of Tissue

The procedure of Example 3 was repeated on additional frozen tissue sections for time periods of 10, 20, 30 and 60 minutes and provided equivalent results.

EXAMPLE 5

Staining of Fixed Tissue

This study was conducted on normal tonsil and nine lymphoma biopsy specimens. Each specimen was sectioned and either fixed in cold acetone alone, or cold acetone followed by 15 minutes fixation in bisulfite as described in Example 4 or fixed in formaldehyde ("Fixative 1, modified Zamboni's). The tissue sections for the study were prepared as described below:

1.) Biopsies are sectioned 6 to 8 $\mu$m in thickness, picked up on clean glass slides, and immediately placed into cold acetone (0°–8° C.) for a minimum of 10 minutes and a maximum of 30 minutes.
2.) Slides are removed from the acetone and allowed to air-dry for a minimum of 10 minutes and a maximum of 1 hour and are placed in a desiccator with desiccant for a maximum of 10 days.
3.) Sections from each biopsy to be stained are removed from the desiccator and labelled with the appropriate slide barcodes for the staining protocol desired.

Frozen sections of tissue prepared as described above were stained according to a standard protocol in a streptavidin DAB Detection Kit (commercially available from Ventana Medical Systems, Inc., Tucson, Ariz., Catalog No. 250-001), following rehydration in the bisulfite tissue fixative for 15 minutes.

The following nineteen (19) antibodies were used as the primary antibodies on each case (group of slides from a single patient): MOPC-21, anti-kappa, anti-lambda, anti-IgM, anti-IgG, anti-CD22, L26, Leu 12, Leu 1, Leu 2, Leu 3, Leu 4, Leu 5, Leu 9, Leu M5, anti-HLA-DR, anti-LCA, Leu-19 and anti-keratin. Each of the antibodies was used at dilutions established previously using acetone-fixed sections which were post fixed on the Ventana 320 instrument with Fixative 1 (modified Zamboni's, a formaldehyde fixative commercially available from Ventana Medical Systems, Inc., Tucson, Ariz., Catalog No. 250-2015).

The tissue was stained according to a standard research protocol used by Ventana Medical Systems, Inc. (the VMSI Protocol #93-18-004). Briefly, a floppy disk which controls the Ventana 320 instrument is inserted into the instrument and the instrument is turned on. The reagents used in the protocol are placed on the reagent wheel and loaded upon the instrument. The sections receiving the tissue fixative of this invention only or the tissue fixative of this invention followed by Endogenous Biotin Blocking Kit treatment to mask biotin present within the sections (commercially available from Ventana Medical Systems, Inc., Tucson, Ariz., Catalog No. 250-050) are immersed in bisulfite fixative for 15 minutes at room temperature.

The bisulfite-treated slides are rinsed in VMSI wash buffer, (commercially available from Ventana Medical Systems, Inc., Tucson, Ariz., Catalog No. 250-050) loaded on the instrument without allowing the tissue to dry, and wetted with VMSI wash buffer. The slides with sections which are not bisulfite-fixed are loaded on the instrument dry. The run is started following standard procedures, as described in the operator's manual. Upon completion of the run, the slides are rinsed, coverslipped, examined microscopically, and the following information is recorded: Date, Case Number, Morphological Preservation, Specific Staining, and Background Staining. Any unexpected unique or background staining are recorded. Tissue was scored on a 0 to 4+ scale with regard to morphologic preservation and specific staining intensity; and from 0 to 2+ for background staining.

The results of the above study documented that it was only the bisulfite fixative that was contributing to the improved morphology and apparent immunoreactivity. Fixing with formaldehyde ("Fixative 1", modified Zamboni's) was inferior, and adding the endogenous biotin blocking reagents did not improve the results. The bisulfite fixative worked well with all antibodies tested.

The above procedure was repeated with lymphoid tissue, cardiac tissue, kidney tissue and liver tissue stained with anti-CD1 and anti-CD11c following bisulfite fixation. The procedure was as described above, with the following exceptions. Liver, kidney, cardiac, and central nervous system tissue are known to have endogenous biotin. Therefore, the endogenous biotin was blocked by the addition of avidin (1 mg/ml) followed by the addition of biotin (1 mg/ml) (Ventana Medical Systems Endogenous Biotin Blocking Kit; Catalog No. 250-050) to such tissues prior to addition of the secondary antibody reagent. In addition, some of these slides were stained using an avidin-horseradish peroxidase conjugate (Vector Laboratories, Burlingame, Calif.; Catalog No. A-2004) in 0.1M phosphate buffer containing 3 mg/ml goat gama globulin (Sigma Chemical Company, Saint Louis, Mo.; Catalog No. C-5860). With each of the tissues, the bisulfite fixative provided superior results in comparison to acetone-fixed specimens.

EXAMPLE 6

Study of Effect of Buffering System

This study compares the ability of tissue fixative prepared as described in Example 1 which was formulated with acetate buffer to a formulation containing citrate buffer to improve staining and morphology of frozen lymphoid sections on the Ventana 320 automated slide stainer. The staining procedure was performed as described in Example 5, (without endogenous biotin blocking).

The citrate formulation was prepared by mixing 24.5 ml of 0.1M sodium citrate with 25.5 ml of 0.1M citric acid. The buffer was brought to 100 ml by the addition of 50 ml of distilled water giving a final molarity of 0.05M and a pH of 4.6. A total of 0.380 gm of sodium metabisulfite (Sigma Chem. Co. Cat. #S9000) was added and the mixture was stirred until the sodium bisulfite was dissolved. The solution was stored in a capped plastic bottle at room temperature.

A total of three lymphomas with normal tonsils as controls were run using the twenty antibodies described in Example 5 on each case. No difference was detected between the two bisulfite fixative formulations.

What is claimed is:

1. A tissue fixative comprising an acidic buffer having a pH of from about 4 to about 5 and, as the sole fixative agent, a bisulfite salt in a concentration of from about 20 mM to about 250 mM.

2. The tissue fixative of claim 1 wherein said bisulfite salt is present in a concentration of from about 20 mM to about 80 mM.

3. The tissue fixative of claim 1 wherein said bisulfite salt is sodium bisulfite.

4. The tissue fixative of claim 1 wherein said acidic buffer is selected from the group consisting of acetate buffer and citrate buffer.

5. The tissue fixative of claim 1 wherein said fixative consists essentially of 40 mm sodium bisulfite in 0.1 M acetate buffer having a pH of from about 4 to about 5.

6. A method of fixing tissue comprising contacting said tissue with a tissue fixative comprising an acidic buffer having a pH of from about 4 to about 5 and, as the sole fixative agent, a bisulfite salt in an effective amount for tissue fixation.

7. The method of claim 6 wherein said bisulfite salt is present in a concentration of from about 10 mM to about 250 mM.

8. The method of claim 6 wherein said tissue is selected from the group consisting of a frozen section, a cytological preparation, and a needle biopsy.

9. The method of claim 6 additionally comprising the step of contacting the tissue section with an antibody.

* * * * *